(12) United States Patent
Postrel

(10) Patent No.: US 12,201,589 B2
(45) Date of Patent: Jan. 21, 2025

(54) ANTI-AGING THERAPY FOR CANINES AND OTHER DOMESTICATED ANIMALS

(71) Applicant: Richard Postrel, Miami Beach, FL (US)

(72) Inventor: Richard Postrel, Miami Beach, FL (US)

( * ) Notice: Subject to any disclaimer, the term of this patent is extended or adjusted under 35 U.S.C. 154(b) by 528 days.

(21) Appl. No.: 17/676,486

(22) Filed: Feb. 21, 2022

(65) Prior Publication Data

US 2022/0175694 A1 Jun. 9, 2022

Related U.S. Application Data

(63) Continuation-in-part of application No. 15/952,230, filed on Apr. 12, 2018, and a continuation-in-part of application No. 17/227,320, filed on Apr. 11, 2021, now Pat. No. 12,115,135, which is a continuation-in-part of application No. 15/952,230, filed on Apr. 12, 2018, and a continuation-in-part of application No. 15/952,226, filed on Apr. 12, 2018, now abandoned.

(60) Provisional application No. 63/151,073, filed on Feb. 19, 2021.

(51) Int. Cl.
| | |
|---|---|
| A61K 31/05 | (2006.01) |
| A23K 10/30 | (2016.01) |
| A23K 20/111 | (2016.01) |
| A23K 20/158 | (2016.01) |
| A23K 20/184 | (2016.01) |
| A23K 50/40 | (2016.01) |
| A61K 31/568 | (2006.01) |
| A61K 36/185 | (2006.01) |
| A61P 5/00 | (2006.01) |

(52) U.S. Cl.
CPC .............. *A61K 31/05* (2013.01); *A23K 10/30* (2016.05); *A23K 20/111* (2016.05); *A23K 20/158* (2016.05); *A23K 20/184* (2016.05); *A23K 50/40* (2016.05); *A61K 31/568* (2013.01); *A61K 36/185* (2013.01); *A61P 5/00* (2018.01)

(58) Field of Classification Search
CPC .... A61K 31/05; A61K 31/192; A61K 31/085; A61K 31/352; A61K 31/566; A23K 20/168; A23K 20/184; A23K 20/111; A23K 20/121
See application file for complete search history.

(56) References Cited

U.S. PATENT DOCUMENTS

| | | | |
|---|---|---|---|
| 8,221,809 B2 * | 7/2012 | Subramanian | A23K 20/179 426/89 |
| 9,480,689 B1 * | 11/2016 | McGlone | A61P 15/08 |
| 2018/0071314 A1 * | 3/2018 | Dunlop | A61P 15/00 |

FOREIGN PATENT DOCUMENTS

| | | | | |
|---|---|---|---|---|
| WO | WO-2020239784 A1 * | 12/2020 | | A61K 31/05 |
| WO | WO-2022173827 A1 * | 8/2022 | | A61K 38/35 |

* cited by examiner

*Primary Examiner* — Yvonne R Abbott-Lewis

(57) ABSTRACT

The present invention discloses a system and method for improving the quality of life in canines and other domesticated animals. As animals age testosterone and other supportive hormones diminish causing reduced activity, a lack of mobility, decreased bone density, and general well-being. Precursor compositions are selected and designed for the purpose of formulating non-toxic therapeutic hormone supplements for oral consumption. The process and method of this invention is comprised of therapies produced from two or more selected non-toxic prohormones that combine during digestion and delivered through a chewable and edible gummy treat. As such there is no requirement for changing the subject's current diet. The present invention features a continuous low dose supplementation to be incorporated daily whereby dosages are correlated according to the subject's age, weight, sex, and breed. The beneficial results of the present invention are achieved through the absorption of the prohormones in the composition into the bloodstream effecting delivery to all cells including those specific cells where the conversion enzymes are activated by the organism's needs. The delivery and transport of inactive prohormones minimizes liver toxicity since the precursors are carried through the hepatic portal system to and through the liver and into general circulation in inactive forms.

19 Claims, No Drawings

ANTI-AGING THERAPY FOR CANINES AND OTHER DOMESTICATED ANIMALS

The present invention discloses a system and method for improving the quality of life in canines and other domesticated animals. As animals age testosterone and other supportive hormones diminish causing reduced activity, a lack of mobility, decreased bone density, and general well-being. Precursor compositions are selected and designed for the purpose of formulating non-toxic therapeutic hormone supplements for oral consumption. The process and method of this invention is comprised of therapies produced from two or more selected non-toxic prohormones that combine during digestion and delivered through a chewable and edible gummy treat. As such there is no requirement for changing the subject's current diet. The present invention features a continuous low dose supplementation to be incorporated daily whereby dosages are correlated according to the subject's age, weight, sex, and breed. The beneficial results of the present invention are achieved through the absorption of the prohormones in the composition into the bloodstream effecting delivery to all cells including those specific cells where the conversion enzymes are activated by the organism's needs. The delivery and transport of inactive prohormones minimizes liver toxicity since the precursors are carried through the hepatic portal system to and through the liver and into general circulation in inactive forms.

This invention avoids deleterious events caused when direct testosterone or testosterone-analogue is processed in the digestive system creating toxicity in the subject's liver. The animal's general quality of life, vigor, and activity are thereby improved. Declines associated with aging including, but not limited to: muscle strength and mass, bone density, blood cell production fat distribution, etc., are mitigated or reversed using the therapeutics of this invention.

As prohormones circulate throughout the body to their site(s) of action, the prohormone is inactive until it reaches a tissue or organ in need that processes or metabolizes both prohormones through one or more enzymatic reactions active at the location(s) where the activity is needed. At these sites the active hormone is formed. The newly formed hormones are locally reactive at the conversion sites when they bind with specific receptors for the newly activated hormone. Undesired stimulation that would result from hormone circulating freely (as would occur when a hormone is injected) is avoided. Toxic build-up, e.g., in the liver, kidney, adrenal gland, etc., is avoided. In accordance with the present invention, toxic encounters in other tissues are avoided along the circulatory pathway.

This precursor delivery process may be enhanced by formulating the therapeutic with an accessory compound that improves or enhances flavor, texture, chewiness, crunchiness, etc. Additional components may be incorporated to control uptake of nutrients in general or in the therapeutic by targeting the cells that line the intestines to guide uptake and stimulate appetite.

As canines and all large animals grow and develop, the maturation process is directed by hormonal communications between the animal's various systems. Different cells in the different tissue systems respond to hormones differently depending on receptors expressed on the cell's surface. The bloodstream delivers either active hormone or a precursor that is enzymatically acted upon locally to produce the specific locally required active hormone compound when needed. The current invention avoids the adverse effects created by hormone injection whereby the circulation delivers the injected hormone throughout the body, which allows the hormone to indiscriminately act at inappropriate sites with resultant undesired or toxic results.

Canines and other mammals are large complex organisms made of trillions of cells. The various cells differentiate to take on different tasks to support survival of the organism of which the cells are members. These cells comprise highly specialized differentiated cells and less differentiated cells that when called upon act as stem cells to produce one or more highly specialized differentiated cell(s). Cells differentiate by selectively activating and de-activating specific genes to maximize each cell's abilities for assigned tasks while leaving other essential functions to other differently specialized cells. The cells specialize by emphasizing certain enzymatic activities and eschewing others. Specialization is accomplished through selective induction of the genes for the specific proteins each individual cell makes and uses. We categorize cells, tissues, enzymes, etc. by assigning and designating them as belonging to one or more systems—i.e., groups interacting to perform related functions.

The digestive or gastrointestinal system is one such collaboration of specialized cells. Food (and drugs) enter through the mouth before progressing through the esophagus, stomach, small intestine and large intestine prior to elimination. Cells lining this system secrete substances to aid digestion including, but not limited to: enzymes, acids, co-factors, bicarbonate, hormone lubricants, water, etc. Cells along the system receive food and chemical signals from digestive cells closer to the mouth. They also are in communication with other systems in the body though hormonal and nerve signaling. Cells in the digestive system both receive and send instructions to other parts of the body to facilitate absorption and delivery of required nutrients into the bloodstream and then to the whole body.

The present invention provides oral compositions that are absorbable and/or metabolizable hormone supplements that can be incorporated into an animal's regular diet to invigorate metabolism and general good health. Each supplemented hormone is provided in an inactive form that is available for conversion by enzymatic activity—at its desired site of action—to a compound (hormone) that stimulates the local androgen receptor. The prohormone delivered into the bloodstream acts as a substrate compound that individual body systems or cells will act upon enzymatically to convert to hormones with one or more activities appropriate to that specific site. Well-known prohormones include dehydroepiandrosterone (DHEA), pregnenolone, androstenedione and androstenediol.

After ingesting compositions of the present invention, the digestive system plays a necessary role in absorbing compounds into intestinal cells and then delivering these inactive prohormone compounds as a beneficial supplement. Optimizing absorption and appropriate delivery to cells that will benefit requires interaction of multiple body systems. As we and all mammals age these signaling pathways break down thereby reducing optimal performance, health and general well-being. Providing supplements that directly replace hormones whose production has reduced or is in the process of being reduced may be beneficial in itself to cells in need. But the general delivery of active hormone throughout the body regardless of local requirements reduces or skews net beneficial effects. The active hormone in circulation is available in a form that is highly active across a large variety of cells, i.e., any cells that express that hormone's receptors regardless of timely needs, and thus will inherently exert broad range, situationally undesired, and potentially toxic effects.

As alternatives to chewier, other means for this therapy may be provided. including, but not limited to: a toothpaste, feed, a spritz, a small crunchy treat, a prescription food product, a spray, an ampule, etc. The preferred embodiment is formulated as a treat that is administered without requirement for altering diet or feed schedule. A gummy treat may be formulated in several sizes corresponding to large, medium, or small dogs, sex, neuter status, breed, etc. Treats may be color or shape coded to indicate strength to distinguish different formulations.

While testosterone and similar androgenic supplementations have seen significant use in body builders as a muscle growth and retention booster in humans, results have been capricious with significant detrimental side effects, at least partially due to erratic, unpredictable intestinal absorption and the untargeted metabolic activities in tissues throughout the body. Detrimental effects have been recognized in many organs, including, but not limited to: liver, kidney, heart, etc. Abnormal cholesterol and other blood lipids, weakened immune system response and autoimmune reactions, hypertension, and severe acne are recognized effects from short term and long term use of these active substances. Use of testosterone and similar steroids is recognized as unsafe, leading to prohibition by many sports bodies, including, but not limited to: Major League Baseball, the NFL, the International Olympics and Para-Olympics, the NCAA, and numerous individual sport regulatory groups. Detrimental effects are also noted in animals. Horses, for example, are tested at all major tracks for use of banned steroid substances. Testosterone and related steroids are listed as Schedule III in the US Controlled Substances Act. While many pro-hormone supplements are generally considered as safe in proper doses, even those approved by regulatory bodies such as the US FDA are considered as dopants that can result in disqualification or suspension in many sports because of recognized performance enhancing effects. Even if considered unfair in competition, pro-hormones such as DHEA have been approved for safe use in humans are therefore quite acceptable for use in animal supplementation.

Two problems are recognized with direct steroid supplementation: a) variable absorption and delivery to the blood dependent on dietary, environmental, behavioral, and genetic factors; and b) uncontrolled delivery and activity throughout the body, i.e., to tissues with current need—as well as tissues where current steroid activity will be counterproductive. While scheduled injections can overcome the absorption inconsistencies, constant frequent injection, —one or more times a day—is not generally feasible. The inconsistent, highly variable sites of action of the active hormone mask or detract from beneficial actions as the hormone is active throughout the body including numerous locations where activity is not needed and may be on-balance harmful to the organism. The present invention obviates the use of injections through its improved and more predictable absorption and delivery of a steroid hormone precursor, in some embodiments, in conjunction with a cannabinoid component. Less psychoactive cannabinoids are preferred so that activity levels are merely increased, not greatly (and possibly unpredictably) changed. The doses required for enhanced uptake might be considered negligible in comparison to some of the "edibles" for humans available in locals where cannabis is legal.

The improved controlled delivery of one or more pro-androgenic stimulants to the bloodstream with subsequent delivery to and deposition at desired locations in the body—where locally expressed enzymes are in control—to effect proper hormone activation, greatly decreases the potential for side-effect damage to the liver, kidneys, adrenal, and other organs or systems. Controlled uptake by the intestines minimizes the time that the gut microbiome changes the chemical makeup of the supplemented compound(s) leading to more targeted and predictable androgenic effects. When a cannabinolic oil or alcohol is used, additional oils, including, but not limited to: vegetable, rapeseed/canola, soy, corn, peppermint, lavender, sandalwood, bergamot, rose, chamomile, ylang-ylang, tea tree, myrcene/hops, jasmine, lemon, etc. may be preferred to improve flavor, but also as a carrier for the supplemented active ingredients. The prohormone and/or cannabinolic supplement compound may be provided as an ester or other modified format to facilitate packaging, shelf-life, delivery to desired portion of the gastrointestinal tract, etc. DHEA is a prohormone for both testosterone and estrogen allowing the body's tissues to process the supplement in the tissues to outcomes specific to the organism and the tissue. DHEA has been approved by the FDA for use by humans. 7-keto-DHEA, and DHEA-S, both naturally occurring metabolites of DHEA, are alternative compounds that may substitute for DHEA or be co-administered. FDA approval is strong endorsement of the safety potential of DHEA precursor hormone in animals.

Anabolic steroids, a class of steroids that includes androgenic compounds such as testosterone and prohormones, e.g., dehydroepiandrosterone (DHEA), pregnenolone, androstenedione, androstenediol, etc., are the steroids known for use by athletes to stimulate growth, increase strength, and allegedly improve athletic performance. These, and in fact all anabolics (steroids or other compounds binding androgen receptors to promote growth), are as a group associated with serious side effects and must be used sparingly, and most definitely not in the extreme doses used in the past by athletes. Steroid use is severely restricted in international competitions, because of the unfair increased strength with less training, but also because of the observed long-term health damage, including, but not limited to: hepatic, endocrine, and reproductive function; tumors of the liver and kidneys; cardiac abnormalities; and psychiatric symptoms.

Testosterone, a primary anabolic steroid, is readily metabolized into dihydrotestosterone in the body by the ubiquitously active 5-α-reductase (5AR) enzyme (dihydrotestosterone is thus a metabolite of testosterone). Nandrolone is a byproduct of the aromatization (conversion) of testosterone into estrogen. Testosterone is an intermediate in natural synthesis of anabolic steroids, e.g., DHT and nandrolone. As discussed above, there are serious downsides to administering testosterone as an injected or ingested metabolic supplement.

Testosterone itself is the principal male sex hormone. Hormones are defined and classified as chemical messengers of the human body, which means that hormones are what carry messages to different cells and tissues in the body to tell those cells and tissues what to do (grow muscle tissue, heal and repair, manufacture important components, perform a specific job, etc.). Without hormones of all different types, functions within the human body will proceed or not proceed unregulated and out of control. How much testosterone the average male produces is dependent on many different factors, which include: individual genetics, age, lifestyle habits, nutritional habits, and activity levels. On average, it has been determined that the median level of testosterone production among 30 year old human ~150-175 lb. males is between 50-70 mg weekly. Where any given individual might land within that range is dependent on the aforementioned factors. It is common knowledge that the most prominent effects of the hormone testosterone appear and are experienced during puberty, which is evidenced by an increase in testosterone production and secretion, and will typically reach the highest endogenous levels at this point in any given man's life. This significant increase in testosterone serves to impart very important physiological changes of the male body. Testosterone governs many different functions within the body. The nature of hormones in the circulation is to govern systemic functions remotely around the body, and testosterone is no exception to this. Dosing can be based on the blood levels of the intended recipient, their weight, the chemical nature of the supplement (bioavailability, half-life, partitioning in body compartments, binding to proteins, etc.) to maintain the animal at an androgen level approximating or preferably exceeding by about 1.5, 2, 2.5 or 3 times the previous average age-reduced levels.

Androgens such as testosterone and DHT bind to androgen receptors (ARs) in cells. The resulting androgen-receptor complex regulates gonadotropin secretion and spermatogenesis. The androgen-receptor complex is responsible also for external vinilization and for most androgen actions during sexual maturation and adult life. DHT is an especially potent androgen because it binds with greater affinity to androgen receptors than testosterone does. Testosterone production in intact mammals is stimulated by luteinizing hormone (LH). It is understood that follicle stimulating hormone (FSH) stimulates testosterone production also. Testosterone concentrations in the blood serum are regulated in part by a negative-feedback pathway in which testosterone inhibits the formation and/or secretion of luteinizing hormone-releasing hormone (LHRH). LHRH acts to stimulate secretion of LH by the pituitary gland. Testosterone acts also by regulating the sensitivity of the pituitary gland to LHRH.

Taking dogs, aka canines, as an example, the present invention provides improved health and longevity for the animal component of the relationships humans are finding more and more significant. Maintaining a pet's well-being can support oxytocin levels in a human owner. Oxytocin is one of the natural inducers of AEA synthetic pathways. Thus, improving pet's activities that lead to oxytocin release in the human owner's body can have a beneficial side-effect of supplementing cannabinoid production and circulating levels in the human owner(s).

Animals exhibit large differences in their mitochondria and mitochondrial activities. These differences may be exacerbated with aging. By optimizing energy metabolism through monitoring and improvement in mitochondrial metabolism, (energy efficiency) the vitality effects observed through androgen balancing may be further enhanced. Accordingly, the invention may include an augmented approach wherein, in conjunction with androgen balancing as an anti-aging measure that optimizes activities and/or in conjunction with system rebalancing by enhancing cannabinoid activities, additional improvement may be obtained by also optimizing mitochondrial activity, metabolism and performance.

Common diseases in the aging dog include: arthritis, which reduces activity levels and may make the animal more irritable or reclusive; reduced bone density, which can lead to fractures; obesity, which can acerbate arthritis and other diseases such as cardiomyopathy and usually reduces animal activity levels; joint dysplasia, which reduces animal comfort and activity; gum disease; diabetes; blindness of various etiologies; dementia; and other diseases of aging familiar in humans. Metabolic functions may be impaired, for example, adipose tissue may experience accelerated or location improper deposition and/or aberrant utilization, glucose metabolism and metabolism of other sugars may be altered though diabetic effects and compensating metabolic shifts.

For example, in humans both free testosterone and total testosterone have been documented in their decline as a male ages. Up to their fifties, human males essentially maintain total testosterone with about a 25% drop in free testosterone from about the age of thirty to about fifty. In the ensuing years both total and free testosterone continue to decline until about the age of eighty the levels are only about half the levels previous to age fifty. While there are differences in effects of aging between mammals, in general testosterone levels decline with age as the animal's vitality also declines. As an approximation, 25% supplementation may be used as augmentation beginning at approximately age 5 in dogs and age 7 in cats. The supplemented amounts will depend on the androgen compound chosen and its comparison in activity to testosterone. Advisedly testosterone levels will continue to be monitored with additional supplementation as Testosterone activity lessens.

Evidence is building that age related reduced testosterone levels in human males, and thus in other mammals, may be related to growth of pot bellies, and possibly, heart attacks, strokes, osteoporosis, clinical depression and some presentations of Alzheimer's disease.

Evidence relating to human females suggests that testosterone levels may be important with regard to depression, activity level and general sense of well-being. There is also evidence that in human females, a testosterone supplement may improve activity levels and maintain a leaner body. Low testosterone levels in human females have been associated with lack of motivation and a sense of fatigue. The common weight gain and increased adipose tissue deposition in women starting approximately 10 years prior to menopause coincides with a commonly observed decreased level of circulating testosterone. This suggests an important component of the present invention relating to maintaining testosterone balance will benefit both male and female mammals, including, but not limited to: canines, equines and felines.

Studies suggest that maintaining an optimized testosterone level as the animal ages can result in improved vigor, reduced injury, and greater activity and possibilities for social interaction. Testosterone is often tested as a marker for steroid hormones generally. Management of circulating testosterone also has the possible effect of preventing or reducing injury, such as muscle or joint injury, and can thereby appear as an anti-aging agent to maintain a higher level of activity available to the animal and to the animal's human companion(s). Effective supplementation in accord with the present invention should result in multiple positive effects throughout the animal.

While "testosterone" level management, and supplementation where warranted, have proved successful in improving specific health effects all over the body, administration has been carefully controlled within the medical community to avoid misuse and deleterious effects that can be associated with elevated testosterone levels that exceed safe limits.

The observation that as testosterone levels decrease during aging and that testosterone is believed to enhance muscle development suggests that the occurrences are not purely coincidence. In fact, muscle tissue expresses androgen receptor (AR) protein so it would be understood that testosterone would influence muscle metabolism. Supporting evidence that testosterone supplementation or replacement increases muscle fiber protein synthesis and that pluripotent stem cells capable of differentiating into muscle fiber cells have high levels of AR expression suggests a causal relationship exists. Accordingly, supplementing androgen, e.g., testosterone to an aging animal may maintain or build muscle mass. Better muscle mass is associated with lower incidences of diabetes so the benefits of testosterone balancing would be expected to cascade through many organs and tissues. But at lower levels of activity while testosterone balance may produce profound benefits an even greater improvement is possible if mitochondrial optimization is partnered with the balancing. Not intending to disparage the invention approach wherein animal health and relationships are augmented by testosterone balancing, the invention recognizes that the augmentation can be amplified by 1) maintaining or optimizing mitochondrial performance as part of the intervention; and/or 2) by taking advantage of cannabinoid compounds to facilitate balancing throughout additional systems. On the other hand, allowing mitochondrial impairment or other systemic imbalances to degrade benefits of androgen balance would be seen as slowing or limiting benefits of the balancing itself. In fact, relating to aging, some believe that oxidative stress of mitochondria may have a major role in age related energy deficit.

Androgenic compound abusers have contributed to testosterone's and other androgenic hormones' shocking disparagement in the news and social media through reports of occasional wild and violent activities. There are also reports of severe health outcomes such as brain tumors, but perhaps, partly related to publicity from these warnings about androgenic misuse and exhibits of "over manliness", steroid supplementation/abuse continues in a significant segment of the population, both male and female. Though abuse may present long term problems for the individual and society, society at large, law enforcement, and politicians can understand that the abuse is a result of testosterone's positive effects.

While some desired effects, for example, increased muscle mass in body builders and other professional athletes, may be valued for their immediate effects, long term effects, for example use over decades, has been shown to increase propensity for heart attack and stroke. The length of administration and the expected remaining lifespan of the individual should be considered before enhancing androgen in the bloodstream.

Other noted effects include elevated LDL and higher LDL/HDL ratio, increased blood pressure, increased cancer, for example, brain and liver, and difficulty in movements that may be caused by excess tissue deposition. Androgen abuse is also associated with testicular wasting or atrophy which in humans may or may not be desired depending on one's desires for fatherhood. In neutered dogs, this of course would not be a relevant concern.

Most of these recognized problems can be avoided or minimized simply by managing testosterone blood levels to levels more prevalent in normal animals or limiting administration to older animals with for example an expected remaining lifespan of about a decade or less. For example, the irritability, aggressive behaviors, rage, violence, delusions, manic eating, etc., appear to be associated with abuse of androgens that involves massive dosing regimens. Liver disease and tumor events appear associated with long term administration of moderate to high doses.

The present invention seeks to avoid these problems by optionally providing systems-wide rebalancing tools in the form of cannabinolic augmentator supplements or facilitators and by monitoring, either through behavioral observation, or potentially by measuring blood, saliva, urine, or skin, androgen or androgenic activity. The reliance on the prohormone minimizes system wide inappropriate effects. Unless behavioral problems become evident testing of blood may not be necessary or recommended. Dosing may be adjusted as the animal ages according to a calendar scheduling or more individualistically through observation of animal behavior. Many owners may opt to start with a low dose that may be increased to achieve desired behavioral effects. When the dosing is easily adjusted, such as when delivered as a food additive, a supplement, a spray, a treat, etc., the owner may have complete control. When delivered in a prepared food, supplements may be added, either to the food itself or by using one of the other mechanisms for delivery. Even minor undesired elevation above a targeted amount, perhaps resulting from metabolic differences, change in food, or a mistake in dosing or formulation can be properly corrected. Long term effects seen over decades may not be a problem at all in shorter lived species. But age may be considered as a factor.

Restoration of testosterone (as a marker for steroid hormones) to approach normal physiological levels can help to restore to a more youthful state and improve the function of many of the different systems where testosterone's effects on the cellular level are accomplished. This includes, for example, action in the bone marrow that increases red blood cell count, which translates to increased endurance, improvement in energy, well-being, and restoration of muscle mass.

There are various studies that have determined where, on average, testosterone levels should be in males according to various age groups. Generally, testosterone in human males declines about 1% per year from the late thirties. For animals, the decline may be steeper depending on size, species and lifespan, and will generally occur at a younger but still at a middle age.

Supplementation in accordance with the present invention may help avoid serious medical problems. For example, osteoarthritis and hip dysplasia are especially common and problematic in larger dog breeds and larger dogs in general. Dogs will reduce activity level and avoid some previous activities to hide the symptoms or to avoid associated pain. Aging is also associated with a general lethargy that can be a result of or mask other diseases such as a failing heart, painful joints, decreased muscle tone, arthritis, etc. and may be a factor in weight gain that can cause or exacerbate other disorders. Increased dysplasia and obesity have been observed to have increased occurrence in canines that have been spayed or neutered. While the benefits, in most cases, necessity of spaying or neutering are profound, the procedure does remove a major source of androgenic hormone, testosterone and its metabolites, from the animal's physiology. While other organs such as the adrenal produce androgens, often the amount decreases as the animal ages and becomes insufficient for optimizing animal activity and health. Similar concerns prevail in cats, but may be less noticed. Vigilance is advised.

While larger dogs appear more prone to hip dysplasia, the outcome is observed in smaller dogs also. Orthopedic Foundation for Animals reports that the top 20 breeds exhibiting dysplasia were: bulldog, pug, dogue de bordeaux, neapolitan mastiff, otterhound, St. Bernard, boerboel clumber spaniel, black Russian terrier, Sussex spaniel, cane corso, basset hound, fila brasileiro, Argentine, dogo, perro de presa canario, American bulldog, Norfolk terrier, Maine coon cat, boykin spaniel, and French bulldog. Clearly this phenomenon is a concern for small as well as large canines. This is not as frequent a concern in cats, but the generally teachings are still applicable.

Most pets and farm and companion animals are spayed or neutered as population control and to avoid undesired behaviors associated with the hormones that drive or control sexual activity, including mate attraction, and other undesired behaviors. But the benefits are deemed to vastly overcompensate for the changes associated with the spaying or neutering. For example, very few farmers maintain a bull; they are dangerous and difficult to control; and especially for dairy herds, artificial insemination produces more reliable timing and product. In pets, male dogs and cats become easier to manage and less aggressive, more homebound, less prone to testicular cancer; females are less prone to breast cancer, will not have repeated heat cycles attracting nuisance male callers and more frequent urination, even indoors, associated with heat to signal receptivity for males. Neutered males are less likely to wander in search of females and less likely to mark territory around and within your house. Steroid supplementation in accordance with this invention can avoid some undesired effects of testosterone while supporting the animal's health.

A trade-off that humans have accepted is that as spayed or neutered animals age, androgenic hormonal support such as provided by testosterone drops off. [Even in intact male and female animals androgenic support declines with aging.] While in male animals the testes would produce the predominant share of androgenic hormone, the feedback mechanisms within the body of a younger animal compensate quite adequately to maintain a general state of health.

But as the creatures naturally age, testosterone activity falls off regardless of the animal's sex or gonadal status. This trend is small but noticeable and has generally been accepted as a part of the aging process. While the declines in animal health are expected and accepted as part of a normal aging process, the decline in performance, comfort, and overall health of the animals can be slowed by persons practicing the present invention.

Though there is variance among breeds of dogs, in general, diminished androgenic influences become apparent between four and eight years of age. Some effects are seen in larger dogs at earlier ages. Some early effects, such as the puppy wildness, which though cute often invokes glee in humans as they recede, and the animal becomes more predictable. These may be related to androgenic stimulants and it will be discretionary whether to begin treating these dogs at this early period or to begin treatment at a stage where animal comfort may be a larger factor. Cats, though not as variable in size, have similar concerns.

Mammalian bodies, like those of dogs, cats, rabbits, etc., have internal means of messaging. Blood flow can be increased or decreased to an area or organ. Nerves sense what is happening at different locations within the body and then transmit information to the central nervous system where multiple inputs are analyzed and coordinated to initiate an output. The output could be neurotransmitter secretion causing a nerve impulse sending instructions to another location in the body. Another very important means of internal commutation is the endocrine system which uses hormones as signaling agents. Hormones are chemicals just as neurotransmitters, but hormones have effect distant from the place of release.

Hormones are chemical messengers used to transfer information through the bloodstream from one part of the body, generally an endocrine gland, to the body in general or to a specific target organ that has a receptor capable of binding or receiving the hormone. Target organs have specialized receptors that gather information that has been transferred from the circulatory system by hormones. An example of a target organ is the uterus, which is stimulated by the circulating hormone estrogen to develop uterine glands. Hormone production—for example, testosterone, estrogen, and progesterone—is regulated by another hormone secreting endocrine gland, the pituitary, at the base of the brain.

Prohormones are building block chemicals used to produce the resultant hormones. In general, the blood levels of sex steroid prohormones are not regulated by any one factor. They are removed from circulation when they bind one of the cells expressing their receptor protein. In contrast, prohormones are generally available to assist in the production of hormones at a site in need that is stimulated by messages in the organism to bind and activate the prohormone, which then act locally or as chemical messengers to other target organs. Injecting a functioning hormone eliminates the problem that may stem from insufficient prohormone, but undermines the natural feedback controls of the body. Increasing circulating prohormone in accord with the present invention thus can result in more balanced supplementation.

The present invention is based in part on the insight that administering one or more androgenic hormones or prohormones to generally healthy appearing animals can increase their overall health and beneficial interactions with nearby humans. In addition, though not as readily observable, achieving an optimal level of circulating hormone may be associated with an increased quality of life, possibly through enhancement of the immune system's ability to defend against bacteria and viruses, to resist cancer, to enhance the circulatory system, and/or to ameliorate undesired stress-responses. Co-administration of compounds active in the cannabinolic systems fine-tunes and facilitates such administrations.

DHEA, a compound with FDA approval for use in humans, is one preferred prohormone for inclusion in products of the present invention. DHEA, aka androstenolone, is an endogenous steroid hormone precursor produced mostly in the adrenal glands, but also in gonads and brain tissue. DHEA is converted to DHEA 3β-sulfate (DHEA-S) by sulfation at the C3β position by the sulfotransferases SULT2A1 and SULT1E1. DHEA-S is more stable in circulation, present in amounts perhaps 250 to 300 times DHEA. DHEA-S thus acts as a reservoir or sink for long term availability of the prohormone. DHEA-S is retro-converted back into DHEA in target peripheral tissues by steroid sulfatase. DHEA/DHEA-S is the most abundant circulating steroid measured in humans. The circulating DHEA serves as a substrate for biosynthesis of androgen and estrogen steroids in the gonads and many other tissues. Potential biological effects of DHEA are reduced by the natural conversion to DHEA-S. DHEA therefore can be fed or supplemented without serious concerns. 7-keto-DHEA is a metabolic product of DHEA that branches off the androgenic pathways. Combinations of DHEA, DHEA-S, and 7-keto-DHEA are used in some embodiments for balanced non-toxic effects. DHEA-S is less absorbable in the intestines than DHEA. Accordingly, when using DHEA-S as a supplement, accessory cannabinolic compounds may be desired to enhance digestive uptake. With this caveat, formulations comprising either DHEA and DHEA-S may be considered for use interchangeably when one of the two is provided or in combination together, optionally with one or more additional prohormone substances.

The compositions used in the present invention are preferably formulated and controllably administered to an animal to induce desired effects without also inducing the undesired side effects that are associated with testosterone and testosterone mimetics—such as undesired anabolic and/or androgenic effects, in the recipient animal. The delivery of the steroid precursor with minimal activity prior to local processing concomitantly with a cannabinoid to enhance food intake and digestive uptake accomplishes these goals.

Dose will depend on the initial status of circulating hormone in the animal, on the active ingredient and its activity within the animal, on the size of the animal, the frequency of dosing and the rate at which an animal would metabolize the active ingredient(s) of the composition. Thus suitable unit doses may range from about: 0.01 mg to 500 mg, e.g., 0.01 mg, 0.05 mg, 0.07 mg, 0.1 mg, 0.15 mg, 0.2 mg. 0.5 mg, 1.0 mg, 2 mg, 3 mg, 5 mg, 7 mg, 10 mg, 20 mg, 25 mg, 30 mg, 50 mg, 75 mg, 100 mg, 120 mg, 150 mg, 175 mg, 200 mg, 250 mg, 300 mg, 350 mg, 400 mg, 450 mg, or 500 mg. Depending on the route of delivery, the animal's size, the animal's age, the animal's gender, the specific composition, etc. other ranges may be relevant, for example, 10 mg-200 mg, 12.5 mg to 150 mg, 15 mg-100 mg, 20 mg-75 mg, 20 mg-50 mg, or 50 mg-100 mg, etc.

Salts, esters, metabolites, protein bound, glycosylated, or matrixed formats of delivery a can be used in the composition, provided they are converted in vitro or in vivo to an active form. Accordingly, the compositions of the invention may comprise pro-hormone that is bound, covalently or non-covalently to a non-hormonal substance.

The compositions, especially when provided as a food, may optionally include additional vitamins or minerals and scents or flavorings or flavor enhancers to render the composition more acceptable to the administering human and/or to the animal. For example, beef, elk, chicken, salmon and/or other scent or flavor appealing to dogs, cats or other pets may be incorporated, a protein binder and/or a vitamin such as one of the B vitamins, e.g., B6 might be added as it or they might be found to help stabilize hormone level. Vitamin D supplements are suitable vehicles for administering the compositions of the present invention.

The composition may be made available in one or more formats including, but not limited to: a capsule, a tablet, an ampule, a caplet, a liquid beverage, a powder, a liquid or powder beverage additive, a gel, a ready-to-eat food, either moist or dry, a chunk, a bar, a toy of desired shape and size. Dried material may be in form of a powder, scraping, flake, a dusting, a grating, an extrusion, etc. Preparation stages may comprise one or more processes selected from the group consisting of: freeze drying, sonication, freezing, heating, spraying, spray coating, printing, encapsulation, enteric coating, dusting, baking, boiling, frying, steaming, air frying, etc. Coatings may be applied to enhance flavor or smell, for identification, for coloring, etc. Preferred embodiments are formulated as chewable treats.

A composition of the present invention may further comprise natural and/or artificial flavoring components, dyes or other coloring additives, preservatives and other conventional food supplement additives known in the art to increase palatability, storage options, etc.

The time and dosage amount administered will vary from animal to animal and will be influenced by the age of the subject, and therefore may be adjusted as the animal ages. It is believed that generally, the younger the animal, the earlier results will be apparent with a smaller dosage amount needed to achieve optimal results. As the animal ages, the composition will have to be administered perhaps more frequently and in larger dosages for the animal to experience optimal results. For example, in younger animals, the pet owner may supplement the animal two or three times per day with only one or two training sessions incorporating a chew supplement of the present invention.

The form of the oral composition can be any suitable form that comprises the active ingredient and allows delivery to the select animal. For example, preferably an animal has been under a veterinarian's care and is general good health. However, the animal is aging and can benefit from receiving a therapeutic intervention that while not strictly necessary for life is beneficial to the animal and its human interactions though optimizing health, for example, by staving off or diminishing arthritis, other bone issues, such as dysplasia, lessening obesity problems and other issues seen in aging animals, such as diabetes, lethargy, pain, etc.

Although the androgen in the oral composition may vary, the method of delivery is also an important factor. For example, DHEA/DHEA-S/7-keto DHEA may be co-administered with an oil, may be admixed in a feed, may be delivered as a toy, etc. The format for delivery is subject to choice of the animal caretakers and is manageable in accordance with this invention. Animals including humans have shown large variations in efficiencies of moving testosterone and other androgens from the gastro-intestinal track to circulation. Given the beneficial effects of supplementation, most desirable effects being observed with approximately a doubling or tripling of typical circulating steroid, in a middle aged or older mammal, monitoring steroid levels in an individual animal may be a consideration in optimizing dosing.

The present invention also includes compositions and methods that combine prohormone compositions with one or more additional therapeutics, such as a vitamin and/or a cannabinoid compound. For example, such additions may be incorporated into or coated on a gummy treat. In some instances the additional cannabinoid compound activates existing cannabinoid receptors found naturally in the gut and interacts with the endocrine and nervous systems to stimulate appetite, digestion, and ingestion. In addition to stimulating appetite, digestion, and ingestion, activating these receptors facilitates absorption of gut contents by these cells further removing the potential for toxicity developing in the subject's liver. Absorption of the prohormone in this fashion is designed to stimulate a more rapid and more controlled delivery through the bloodstream. Potential worries regarding cannabinoid effects in general circulation are minimized since the cannabinolic compounds bind to receptors on the intestinal cells and are only active there, not in general circulation.

Cannabinoids may be used serially or coincident with corticosteroid or mitochondrial augmentation or rebalancing. i.e., they may be provided as distinct chewier or preferably a chewy can be formulated with the full array. The skilled artisan will be cognizant of the cannabinoid involvement in corticosteroid synthesis and release. When administration of one class is varied, effects of the other classes may benefit from dosage or timing adjustment.

In accordance with several embodiments of the present invention, absorption from the gastrointestinal tract is facilitated in both timing and magnitude by utilizing the body's extensive endocannabinoid receptor signaling system.

Distinct types of cannabinoid receptors can be found in different cells and tissues throughout the body. The gastro-intestinal system employs several cannabinoid receptors, most commonly members of the class G-Protein-coupled Receptors (GPR or GPCR) transmembrane proteins. These receptors span the plasma membrane and interact with a GTP-coupled internal protein when stimulated by extracellular ligands. Cannabinoid receptors, CB1 and CB2 are two well-known members in this class of receptors. Numerous additional GPRs (or GPCRs) have been shown to act when bound by one or more cannabinolic ligands. GPR55 and PPARα are two additional well-known examples of endocannabinoid receptors with digestive activities.

Careful and predictable controlled administration of steroid supplementation should be of interest to pet owners. Cannabinoids, while themselves being banned in sports (as performance enhancing drugs), are not as a class considered deleterious to human or animal health when cautiously administered or taken in proper doses.

In the intestine, the endocannabinoid system (ECS) is an important lipid based signaling and immunomodulator system. Lipophilic compounds, those that can readily cross plasma membranes are prime activators of these endocannabinoid pathways. Research relating to medical uses of marijuana and traditional medicines has shown that compounds that bind CB1 and CB2 participate in modulating many physiological responses including, but not limited to: appetite, respiration, metabolism, transmembrane stimulation, nutrient uptake, inflammation, allergy, pain, neurotransmission, etc. These receptors are active in controlling lipid and other nutrient uptake.

The ECS is comprised of G-protein coupled receptors (GPCRs) including, but not limited to human: CB1, CB2, TRPV1, TRPV2, TRPV3, TRPV4, TRPA1, TRPM8, GPR55, GPR118, GPR119, etc. and the animal homologues of similar activity but sometimes different names. The present invention incorporates beneficial effects of cannabinoids, especially the anti-inflammatory, nutrient uptake, and metabolic enhancement effects, to stimulate and predictably control prohormone uptake by intestinal cells.

The native cannabinoid receptor ligands aka "endocannabinoids" are classically represented by arachidonylethanolamide (anandamide, AEA) and 2-arachidonoylglycerol (2AG). Tissue levels of endocannabinoids are maintained by the balance between biosynthesis (e.g., phospholipase D and diacylglycerol lipase-dependent and other pathways), cellular uptake and degradation by enzymes principally, but not limited to: fatty acid amide hydrolase (FAAH) and/or monoacylglycerol lipases (MAGL). Since the discovery of CB1 and CB2 GPCRs such as GPR18, GPR55, GPR119 and the TRPs have been recognized as members of the cannabinoid family. Two notable catabolic enzymes, fatty acid amide hydrolase (FAAH) and monoglycerol lipase (MAGL), are involved in the breakdown of anandamide and 2AG, respectively. Simply put, less FAAH and MAGL means more AEA and 2AG. So, inhibitors of these catabolic enzymes, for example, by nutmeg extracts, may be incorporated into supplements or foods of the present invention to raise active the levels of AEA and 2AG and to generally boost cannabinoid receptor signaling. FAAH and MAGL inhibition therefore can be effective in improving food uptake, but also in reducing or managing pain, anxiety, hypertension and various inflammatory conditions. Nutmeg extracts and food substances of similar activities are therefore optional components for inclusion in the products of the present invention.

The "cannabinoid" (a term indicating cannabis-like activity) compounds have diverse effects, including most notably, some psychoactive effects, became known as phyto-cannabinoids based on their similarities to compounds found in the cannabis genus. The endo/phyto-cannabinoids include but are not limited to: N-acylethanolami(n/d)es which include N-arachidonoylethanolamine (better known as anandamide or more simply AEA), N-palmitoylethanolamine (PEA), N-linoleoylethanolamide (LEA) and N-oleoylethanolamine (OEA).

Since living organisms share many common metabolic paths and features, many mammalian endocannabinoids can be found in other species, including plant species. For example, OEA and LEA are in cocoa; black truffles when grown under certain circumstances contain high levels of AEA. Naturally sourced minimally processed cannabinoids, extracted cannabinoids, modified cannabinoids, and synthetic cannabinoids may be selected for use in the present invention. For example, some pet owners prefer organic or natural components for themselves and/or their pets.

Maintaining AEA activity and preventing its metabolism in the body to form damaging inflammatory substances is a powerful tool for comfort and healthful well-being. COX inhibition can limit prostaglandin D2 ethanolamide formation. A selective COX inhibitor is one approach when constraints are preferred or when other COX-1 or COX-2 pathways are favorably spared. The CDHR3 downstream effects can also be maintained with FAAH inhibition. In many examples both COX inhibition and FAAH inhibition are used.

Phytochemicals (substances found in plants or derivatives of the plant chemicals) or the plants themselves, have been recognized to possess biological activities in traditional medical practices. Several classes of compounds with similarities in structure and/or activities to the THC purported active ingredient of the marijuana source plant have been identified. These are available in several plants outside the *Cannabis* genus and can be, cultured (e.g., through selective breeding or genetic engineering), extracted, purified or synthesized chemically de novo or from derivatives. Such compounds including, but not limited to:

Cannabigerol class: cannabigerolic acid (CBGA) (antibiotic); cannabigerolic acid monomethylether (CBGAM); cannabigerol (CBG) (antibiotic, antifungal, anti-inflammatory, analgesic); Cannabigerol monomethylether (CBGM); cannabigerovarinic acid (CBGVA); Cannabigerovarin (CBGV).

Cannabichromene class: Cannabichromenic acid (CBCA); Cannabichromene (CBC) (anti-biotic, antifungal, anti-inflammatory, analgesic); Cannabichromevarinic acid (CBCVA); Cannabichromevarin (CBCV); Cannabidiolic acid (CBDA) (antibiotic); Cannabidiol (CBD) ((antioxidant, anxiolytic, antispasmodic, antiinflammatory, analgesic); cannabidiol monomethylether (CBDM); cannabidiol C4 (CBD-C4); cannabidivarinic acid (CBDVA); cannabidivarin (CBDV); cannabidiorcol (CBD-C1); $\Delta^9$-tetrahydrocannabinolic acid A (THCA-A); $\Delta^9$-tetrahydrocannabinolic acid B (THCA-B); 6a,10a-trans-6a,7,8,10a-tetrahydro-6,6,9-trimethyl-3-pentyl-6H-dibenzo[b,d]pyran-1-ol, ($\Delta^9$ tetrahydrocannabino-, THC) (analgesic, antioxidant, antiemetic, anti-inflammation); Δ9-tetrahydrocannabinolic acid-C4 (THCA-C4); $\Delta^9$-tetrahydrocannabinol-C4 (THC-C4); $\Delta^9$-tetrahydrocannabivarinic acid (THCVA); $\Delta^9$-tetrahydrocannabivarinic (THCV); $\Delta^7$-cis-isotetrahydrocannabivarin; $\Delta^9$-tetrahydrocannabiorcolic acid (THCA-C1); tetrahydrocannabiorcol (THC-C1).

$\Delta^8$-tetrahydrocannabinol class: $\Delta^8$-tetrahydrocannabinolic acid ($\Delta^8$-TCA); $\Delta^8$-tetrahydrocannabinol ($\Delta^8$-THC).

Cannabicyclol class: cannabicyclol (CBL); cannabicyclolicacid (CBLA); cannabicyclovarin (CBLV).

Cannabieson class: cannabiesoic acid A (CBEA-A); cannabiesoic acid B (CBEA-B); cannabieson (CBE).

Cannabinol and cannabinodiol class: cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabinidivarin (CBDV).

Cannabitriol class: cannabitriol (CBT); 10-Ethoxy-9-hydroxy-Δ-6a-tetrahydro-cannabinol (10-EHDT); 8,9-dihydroxy-delta-6a-tetrahydrocannabinol (8,9-DHDT); cannabitriolvarin (CBTV); ethoxy-cannabitriolvarin (CBTVE).

Miscellaneous class: dehydrocannabifuran (DCBF); cannabifuran (CBF); cannabi-chromanon (CBCN); cannabicitran (CBT); 10-oxo-Δ-6a-tetrahydrocannabinol (OTHC); $\Delta^9$-cis-tetrahydrocannabinol (cis-THC); 3,4,5,6-tetrahydro-7-hydroxy-α-α-2-trimethy1-9-n-propyl-2,6-methano-2H-1-benzoxocin-5-methanol (2H-iso-HHCV); cannabiripsol (CBR); Trihydroxy-$\Delta^9$-tetrahydrocannabinol (triOH-THC).

LEA, PEA and OEA will bind to one or more of the endogenous cannabinoid receptors, but they are also important because they maintain AEA activity through their inhibition of the FAAH enzyme that is responsible for degrading AEA. N-alkylamides exert selective effects on the CB2, and have been shown to exert anti-inflammatory effects similar to AEA. Echinacea contains multiple N-alkylamides that have mimetic effects.

Phytoalkanes, another class of chemical compounds found in various plants, also have demonstrated cannabinolic modulation traits, e.g., n-alkanes ranging from C9 to C39, 2-methyl-, 3-methyl-, and some dimethyl alkanes are common in spices such as curcumin. The major alkane present in an essential oil obtained by extraction and steam distillation was the n-C29 alkane nonacosane (55.8 and 10.7%, respectively). Other abundant alkanes were heptacosane, 2,6-dimethyltetradecane, pentacosane, hexacosane, and hentriacontane. Curcumin reduces liver fibrosis by modulating cannabinoid receptor transmission.

In general, many plant species, especially those used for spices have anti-allergy/anti-inflammatory activities. E.g., nutmeg interacts with the endocannabinoid system by inhibiting certain key enzymes that catabolize (break down) the two main endocannabinoids, anandamide and 2AG.

β-caryophyllene, a phytocannabinoid, and/or its oxides act as full agonists of the CB2-receptor where they exert anti-inflammatory and analgesic effects that are mediated through CB2, but not CB1. Another phytocannabinoid, salvinorin A, from the plant species Salvia divinorum extract is a terpenoid that interacts with a cannabinoid receptor, not yet characterized that apparently forms only in inflammatory conditions. This uncharacterized receptor also acts as a κ-opioid receptor. Many sages produce similar compounds with some activity, but whose activities have not been followed in detail to identify receptor interactions. Myrcene is a major constituent of the essential oil of hops and appears to be related to opioid "high" possibly by agonizing opioid receptors or possibly by antagonizing opioid degradation. Plant sources are hops, verbana and cannabis. Myrcene is also found in lemongrass, thyme and mango. Echinacea contains multiple N-alkylamides that have cannabinoid mimetic effects.

The Helichrysum umbraculigerum, aka woolly umbrella Helichrysum or kerriekruie in Afrikaans, is a fast growing perennial herb with a strong mood-stabilizing and anti-depressant effect due to high concentrations of cannabigerol (CBG). Liverwort contains large amounts of perrottetinenic acid, a THC, mimetic that binds CB1. The cacao plant has endocannabinoid activity by deactivating the FAAH enzyme thereby maintaining AEA levels and levels of similarly active fatty acid derived molecules. FAAH inhibition combines anti-inflammatory effects of several N-acylethanolamines while it targets additional receptors such as TRPV1 and peroxisome proliferator activated receptors.

While synthetic cannabinoids should be used with care in frequency and volume of dosing, one characteristic of the cannabinolic systems is that they are fantastic self-regulators. For example, exogenous AEA and similar phytocompounds that bind endogenous receptors set in motion pathways to rebalance ad restore cannabinoid metabolisms including related pathways for inducing receptors synthetic enzymes and even the degradative enzymes. Small frequent doses can be all the organism requires for superbly balanced cannabinolic controls.

Cannabinoids may be used serially or coincident with corticosteroid or mitochondrial augmentation or rebalancing. The skilled artisan will be cognizant of the cannabinoid involvement in corticosteroid synthesis and release. When administration of one class is varied, the other classes may benefit from dosage or timing adjustment.

Combined interventions involving two or more episodes of redirecting/rebalancing immune/allergy activity, balancing androgen levels in circulation improving animal activity and outlook by optimizing mitochondrial activities will allow even more robust human-animal interaction and better outcomes for the participants. Mitochondrial activities may be simply improved though the cannabinolic component in the composition of the invention which has a dual effect of stimulating appetite and enhancing intestinal uptake of the prohormone.

Examples may further feature a compound that has or supports cannabinolic activity perhaps with presence of an endocannabinoid substance. Activity of such compound may be effected through a G-protein coupled receptor such as CB1, CB2, TRPV1, TRPV2, TRPV3, TRPV4, TRPA1, TRPM8, GPR18, GPR55, GPR118 and/or GPR119.

Cannabinolic activity may reside in, for example, an endogenous mammalian cannabinoid, a phytocannabinoid and/or a synthetic cannabinoid including but not limited to: AEA, 2AG, PEA, OEA, LEA, URB597, URB937, AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, Cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A,KML29, MAFP, MJN110, ML30, N-arachidonoyl maleimide, OL-135, OL92, PF-04457845, SA-57, ST4070, URB880, URB937, indomethacin, MK-886, resveratrol, cis-resveratrol, aspirin, COX-1 inhibitor II, loganin, tenidap, SC560, FR 122047 hydrochloride, valeryl salicylate, FR122047 hydrate, ibuprofen, TFAP, 6-methoxy-2-naphthylacetic acid, meloxicam, APHS, etodolac, meloxicam, meloxicam sodium salt, N-(4-acetamidophenyl)indomethacin amide, N-(2-phenylethyl)indomethacin amide, N-(3-pyridyl)indomethacin amide, indomethacin heptyl ester, SC236, sulinac, sulindac sulfide, pravadoline, naproxen, naproxen sodium salt, meclofenamate sodium, ibupropfen, S-ibuprofen, piroxicam, ketoprofen, S-ketoprofen, R-ibuprofen, Ebselen, ETYA, diclofenac, diclofenac diethylamine, flurbiprofen, fexofenadine, Pterostilbene, Pterocarpus marsupium, 9,12- octadecadiynoic acid, Ketorolac (tromethamine salt), NO-indomethacin, S-flurbiprofen, sedanolide, green tea extract (e.g., epicatechin), licofelone, lornoxicam, rac ibuprofen-d3, ampirxicam, zaltoprofen, 7-(trifluoromethyl)1H-indole-2,3-dione, aceclofenac, acetylsalicylic acid-d4, S-ibuprofen lysinate, loxoprofen, CAY10589, ZLJ-6, isoicam, dipyrone, YS121, MEG (mercaptoethylguanidine), etc.

Such cannabinoids may be identified as members of a class such as: cannabigerol class, cannabichromene class, cannabicyclol class, $\Delta^8$-tetrahydrocannabinol class, cannabieson class, cannabinol and cannabinodiol class, cannabitriol class and miscellaneous class.

Popular compositions used to practice the invention may include one or more cannabinoids selected from the group consisting of: CBGA, CBGAM, CBG, CBGM; CBGVA, CBGV, CBCA, CBC, CBCVA, CBCV, CBDA, CBD, CBDM, CBD-C4, CBDVA, CBDV, CBD-C1, THCA-A, THCA-B, 6a,10a-trans-6a,7,8,10a-tetrahydro-6,6,9- trimethyl-3-pentyl-6H-dibenzo[b,d]pyran-1-ol, THC,) THCA-C4, THC-C4, THCVA, THCV, $\Delta^7$-cis-isotetrahydrocannabivarin, THCA-C1, THC-C1, $\Delta^8$-TCA, $\Delta^8$-THC, CBL, CBLA, CBLV, CBEA-A, CBEA-B, CBE, CBNA, CBN, CBNM, CBN-C4, CBV, CBN-C2, CBN-C1), CBND, CBDV, CBT, 10-EHDT, 8,9-DHDT, CBTV, CBTVE, DCBF, CBF, CBCN, CBT, OTHC, cis-THC, 2H-iso-HHCV, CBR and triOH-THC.

Some practices of the invention can feature metabolism directive or accessory compounds or metabolically active compounds including, but not limited to: an FAAH inhibitor, R-WIN 55,212-2, a MAGL inhibitor, an EFA, oxytocin, $\omega$-3 fatty acid, $\omega$-6 fatty acid.

EXAMPLE 1

For example, a five year old canine (age dependent on the breed, the animal size, etc.) is evaluated at its annual visit. This visit includes a hormonal profile as well as questioning the dog owner about the animal's activities and general health. The veterinarian observes that is common at this age for this type of dog, testosterone levels are continuing to drop and that the dog might benefit from restoring circulating levels of testosterone or other androgenic hormone in the blood.

The veterinarian calculates a target testosterone level and suggests simple oral supplements of DHEA that can help the dog achieve these levels and to thereby pep up the dog to increase enjoyment of the dog and human associates. The prohormone is co-administered with a cannabinoid, e.g., cannabidiol, which facilitates uptake in the gut and results in more predictable outcomes.

The owner chooses from a brochure provided by the veterinarian one of the compositions of the present invention. In fact, the owner here wishes for variety and chooses a relatively hard chew toy, a gel format wherein the composition is encapsulated in a soft, bone shaped, gum like format that the owner believes her kids will enjoy giving the dog. She also takes a small food packet as a sample. This packet has two pouches and a small distribution device where a small quantifiable (by counting or volume measurement) portion (preferably slightly color coded for the human) can be admixed in prescribed proportion with the larger pouch contents to achieve the desired caloric intake and hormonal supplement dosage.

EXAMPLE 2

For example, a seven-year-old canine (a 62 pound poodle) is evaluated at its annual visit. This visit includes a hormonal profile as well as questioning the dog owner about the animal's activities and general health. The veterinarian observes that is common at this age for this type of dog, testosterone levels are continuing to drop and that the dog might benefit from restoring circulating levels of testosterone or other androgenic hormones in the blood.

The veterinarian calculates a target stimulus level using DHEA as the deliverable androgen (prohormone) and suggests simple oral supplements that can help the dog achieve these levels and to thereby restore activity levels in this poodle, and improve interactions between the dog, the dog's owner, and the dog's family.

The owner chooses from a brochure provided by the veterinarian one of the compositions of the present invention. In fact, the owner here wishes for variety and chooses a relatively easy to deliver food supplement in a liquid format dispensable with a simple dropper. The owner also leaves with a card of treats individually marked by time of day and day of week with the designation "For large dogs (greater than 50 lbs.)". This packet has two punches per day which meets the owner's schedule. One punch, 3 punch, and 4 punch packets were available. But the owner was most pleased with the two-punch version. Each punch comprises a combined supplemental composition that incorporates the androgenic Improving compound, DHEA, along with a cannabinoid that will facilitate and steady absorption in the gastrointestinal system.

Combined interventions involving two or more episodes of redirecting/rebalancing immune/allergy activity, balancing androgen levels in circulation improving animal activity and outlook by optimizing mitochondrial activities will allow even more robust human-animal interaction and better outcomes for the participants. Mitochondrial activities may be simply improved though the cannabinolic component in the composition of the invention which has a dual effect of stimulating appetite and enhancing intestinal uptake of the prohormone.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting. Although for simplicity in drafting the claims below are drafted in a manner where each dependent claim specifically asserts dependent status with only a single claim, the reader is put on notice that for purpose of disclosure every claim that references a preceding claim also implicitly is understood to have alternate dependency to all claims ultimately depending from the same claim or claims.

Of course, the reader will recognize that this implicit understanding will not be stretched ridiculously to the extent that a claim might depend from itself. Other features and advantages of the invention will be apparent from the description and claims of the present specification, referenced materials and the present state of the art.

Examples useful in practicing this invention may include a composition or using a composition that improves a human's a non-human animal's well-being that may include, contain or comprise an orally or subcutaneously administrable substance having at least one dosage selected from the group consisting of: a mitochondrial booster, an androgen hormone and a prohormone, said dosage selected to optimize at least one physiologic function in a selected mammal.

Examples may further feature a compound that has or supports cannabinolic activity perhaps with presence of an endocannabinoid substance. Activity of such compound may be effected through a G-protein coupled receptor such as CB1, CB2, TRPV1, TRPV2, TRPV3, TRPV4, TRPA1, TRPM8, GPR18, GPR55, GPR118 and/or GPR119. Antioxidant activity may be featured in one or more or the constituents formulated into the product composition.

Cannabinolic activity may reside in, for example, an endogenous mammalian cannabinoid, a phytocannabinoid and/or a synthetic cannabinoid including but not limited to: AEA, 2AG, PEA, OEA, LEA, URB597, URB937, AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, Cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A, KML29, MAFP, MJN110, ML30, N-arachidonoyl maleimide, OL-135, OL92, PF-04457845, SA-57, ST4070, URB880, URB937, indomethacin, MK-886, resveratrol, cis-resveratrol, aspirin, COX-1 inhibitor II, loganin, tenidap, SC560, FR 122047 hydrochloride, valeryl salicylate, FR122047 hydrate, ibuprofen, TFAP, 6-methoxy-2-naphthylacetic acid, meloxicam, APHS, etodolac, meloxicam, meloxicam sodium salt, N-(4-acetamidophenyl)indomethacin amide, N-(2-phenylethyl)indomethacin amide, N-(3-pyridyl)indomethacin amide, indomethacin heptyl ester, SC236, sulinac, sulindac sulfide, pravadoline, naproxen, naproxen sodium salt, meclofenamate sodium, ibupropfen, S-ibuprofen, piroxicam, ketoprofen, S-ketoprofen, R-ibuprofen, Ebselen, ETYA, diclofenac, diclofenac diethylamine, flurbiprofen, fexofenadine, Pterostilbene, Pterocarpus marsupium, 9,12-octadecadiynoic acid, Ketorolac (tromethamine salt), NO-indomethacin, S-flurbiprofen, sedanolide, green tea extract (e.g., epicatechin), licofelone, lornoxicam, rac ibuprofen-d3, ampirxicam, zaltoprofen, 7-(trifluoromethyl)1H-indole-2,3-dione, aceclofenac, acetylsalicylic acid-d4, S-ibuprofen lysinate, loxoprofen, CAY10589, ZLJ-6, isoicam, dipyrone, YS121, MEG (mercaptoethylguanidine), etc.

Such cannabinoids may be identified as members of a class such as: cannabigerol class, cannabichromene class, cannabicyclol class, $\Delta^8$-tetrahydrocannabinol class, cannabieson class, cannabinol and cannabinodiol class, cannabitriol class and miscellaneous class.

Popular compositions used to practice the invention may include one or more cannabinoids selected from the group consisting of: CBGA, CBGAM, CBG, CBGM; CBGVA, CBGV, CBCA, CBC, CBCVA, CBCV, CBDA, CBD, CBDM, CBD-C4, CBDVA, CBDV, CBD-C1, THCA-A, THCA-B, 6a,10a-trans-6a,7,8,10a-tetrahydro-6,6,9-trimethyl-3-pentyl-6H-dibenzo[b,d]pyran-1-ol, THC,) THCA-C4, THC-C4, THCVA, THCV, $\Delta^7$-cis-isotetrahydrocannabivarin, THCA-C1, THC-C1, $\Delta^8$-TCA, $\Delta^8$-THC, CBL, CBLA, CBLV, CBEA-A, CBEA-B, CBE, CBNA, CBN, CBNM, CBN-C4, CBV, CBN-C2, CBN-C1), CBND, CBDV, CBT, 10-EHDT, 8,9-DHDT, CBTV, CBTVE, DCBF, CBF, CBCN, CBT, OTHC, cis-THC, 2H-iso-HHCV, CBR and triOH-THC.

Some practices of the invention can feature metabolism directive or accessory compounds or metabolically active compounds including, but not limited to: an FAAH inhibitor, R-WIN 55,212-2, a MAGL inhibitor, an EFA, oxytocin, ω-3 fatty acid, ω-6 fatty acid.

Some formulations may feature, for example, N-alkylamides, phytoalkanes, n-alkanes, N-acylethanolamines, flavonoids, curcuminoids, polyphenols, biphenyl neolignans, sesqui-terpenes, N-Isobutylamides and/or p-hydroxyphenyl-O-arylcarbamates, whose carbon presence in the molecule of interest may be specific or in a range where each molecule comprises from 9 to 39 carbon atoms, for example, 9, 10, 11, 12, 13, 14,15,16,17, 18, 19, 20, 21, 22,23, 24, 25,26,27, 28, 29, 30, 31, 32, 33, 34, 35, 36, 37, 38 and/or 39 C/molecule.

Carbon chains may include branches with preferred compounds expected to feature 2-methyl-, 3-methyl-, and dimethyl attachments. Nonacosane, heptacosane, 2,6-dimethyltetra-decane, pentacosane, hexacosane, and hentriacontane are examples of useful carbon chains.

Phyto molecules are featured in some embodiments of this invention. A composition may thus feature parts or extracts, for example, of one of more sources derived from *Echinacea, Echinacea purpurea, Echinacea angustifolia,* curcurmin, *Salvia divinorum*, sage, lemon grass, hops, verbana, *Cannabis*, thyme, mango, *Helichrysum umbraculigerum* liverwort, cacao, ginger, tumeric, *Curcuma longa, Magnolia officinalis*, Norway spruce, black pepper, basil, *Myristica fragrans*, cloves, *Sciadopitys verticillata*, oregano, cinnamon, black pepper, hemp, rosemary, flax, *Elettaria repens*, etc.

Phyto- or phyto mimic compounds/molecules may include but are not limited to: abinene, α-pinene, 4,8-dimethyl-1,7-nonadien-4-ol, 2-hydroxy-4-methyl-valeric, acid, methyl, ester, octanal, O-cymene, eucalyptol, α-phellandrene, cis-sabinene, hydroxide, myrcenol, terpinen-4-ol, α-terpineol, β-thujene, ç-terpinene, trans-α-ocimene, carveol, β-citral, guanidine, geraniol, bornyl, acetate, β-pinene, thymol, geranic, acid, methyl, ester, α-terpinyl, acetate, d-limonene, eugenol, geranyl, acetate, dihydrocarvyl, acetate, α-ylangene, cis-dodec-5-enal, 3-phenyl-2-propenoic, acid, methyl, ester, β-elemene, c, vanillin, epoxy-α-terpenyl, acetate, butanoic, acid, 2-methyl-, 3,7-dimethyl-2, 6-octadienyl, ester, 1-methyl-4-(1-acetoxy-1-methylethyl)-cyclohex-2-enol, 1,2,3,4,4a,5,6,8a-octahydro-4a,8-dimethyl-2-(1-methylethenyl)-, [2r-(2à,4aà,8aá)]-naphthalene, p-mentha-1(7),8-dien-2-ol, ç-muurolene, hydroxy-α-terpenyl, acetate, nerolidol, geranyl, bromide, (−)-α-panasinsen, pyrocatechol, ç-elemene, 9,10-dehydro-isolongifolene, à-calacorene, cis-verbenol, acetic, acid, 1-methyl-1-(4-methyl-5-oxo-cyclohex-3-enyl)ethyl, ester, alloaromadendrene, z,z-2,6-dimethyl-3,5,7-octatriene-2-ol, 4-epi-cubedol, 2-oxabicyclo[2.2.2]octan-6-ol, 1,3,3-trimethyl-acetate, patchoulane, farnesol, caryophyllene, oxide, cis-lanceol, ledene, oxide-(ii), farnesol, acetate, 6-epi-shyobunol, falcarinol, phytol, aromadendrene, oxide-(2), heptacosane, longipinene, epoxide, hentriacontane, decamethylcyclopentasiloxane, geranyl, isobutyr, hexamethylcyclotrisiloxane, 1-docosene, tetratetracontane, dodecamethyl-cyclohexasiloxane, etc.

Supplemental components used to modify or to improve more rudimentary formulations or compositions may comprise, but are not limited to: β-caryophyllene, a β-caryophyllene oxide, salvinorin A, myrcene, perrottetinenic acid, apigenin, quercetin, cannflavin A, cannflavin B, β-sitosterol, vitexin, isovitexin, kaempferol, luteolin, orientin, a gingerol, capsaicin, curcumin, demethoxycurcumin, bisdemethoxycurcumin, cyclocurcumin, trans-resveratrol, diferuloylmethane, trans-arachidins, trans-piceatannol, isoprenylated trans-resveratrol derivatives, sciadonic acid magnolol, honokiol, malyngamide B, (+) sabinene, (−) sabinene, lsobutylamide, dodeca-2E,4E-dienoic acid isobutylamide, dodeca-2E,4E, 8Z,10Z-tetraenoic acid alkylamide, 1-[(2E,4E,8Z)-tetradecatrienoyl] piperidine, β-caryophyllene, ajulemic acid, etc.

Compositions are not limited to classic medicament shapes or formats. For example, a gel, a powder, a toy, a liquid, a food supplement, a moist food, a dry food, a small treat, a solidified matrix, etc., may be used for delivery. A 3-D printer may be applied to control dosing of the featured components, e.g., a hormone or prohormone, Delayed-release shaped constructs, a chewable toy-shaped substance, e.g., a doggie bone, a dinosaur, a cat, a mouse, a squirrel, a rodent, a ring, a fist, a bow, a ball, etc. One or more formats may feature a plurality of packagings, wherein at least a first packaging contains active ingredient for admixing to at least a second package contents.

The invention claimed is:

1. A composition comprising a first and a second androgenic prohormone wherein at least one of said first and said second androgenic prohormone is selected from the group consisting of: DHEA, 7-keto DHEA, pregnenolone, androstenedione, androstenediol, and DHEA-S.

2. The composition of claim 1 wherein at least one of said first and said second androgenic prohormone is selected from the group consisting of: DHEA, 7-keto DHEA, and DHEA-S.

3. The composition of claim 1 further comprising an oil selected from the group consisting of: vegetable, rapeseed/canola, soy, corn, peppermint, lavender, sandalwood, bergamot, rose, chamomile, ylang-ylang, tea tree, myrcene/hops, jasmine, and lemon.

4. The composition of claim 1 further comprising nutmeg or nutmeg extract.

5. The composition of claim 1 formulated as an oral preparation formulated as a chewable edible treat.

6. The composition of claim 1 formulated as an oral preparation selected from the group consisting of: an animal feed, a food supplement, a prescription food product, a spray, an ampule, a supplemented rawhide, a vitamin D supplement, and a chew toy.

7. The composition of claim 1 formulated as a feed supplement, said supplement in a format selected from the group consisting of: a gel, a powder, a liquid, a grating, a strip, an ampule, a tablet, and a capsule.

8. A composition comprising a first and a second androgenic prohormone further comprising a compound that binds and stimulates a mammalian endocannabinoid receptor.

9. The composition of claim 8 wherein DHEA-S at least one of said first and said second androgenic prohormone comprises DHEA-S.

10. The composition of claim 8 wherein said endogenous endocannabinoid receptor is selected from the group consisting of: CB1, CB2, TRPV1, TRPV2, TRPV3, TRPV4, TRPA1, TRPM8, GPR18, GPR119, GPR55, GPR118 and analogues thereto.

11. The composition of claim 10 wherein said compound that binds and stimulates a mammalian endocannabinoid receptor comprises a member of a class selected from the group consisting of: cannabigerol class, cannabichromene class, cannabicyclol class, $\Delta^8$-tetrahydrocannabinol class, cannabieson class, cannabinol and cannabinodiol class, cannabitriol class, and miscellaneous class.

12. The composition of claim 11 wherein said compound that binds and stimulates a mammalian endocannabinoid receptor comprises a member of the cannabinol and cannabinodiol class.

13. The composition of claim 11 wherein said compound that binds and stimulates a mammalian endocannabinoid receptor comprises a member of the Cannabichromene class.

14. The composition of claim 8 wherein said compound that binds and stimulates a mammalian endocannabinoid receptor comprises a compound selected from the group consisting of: cannabidiolic acid (CBDA), cannabidiol (CBD), cannabidiol monomethylether (CBDM), cannabidiol C4 (CBD-C4), and cannabidivarinic acid (CBDVA).

15. A method for providing a safe therapeutic composition to a canine, said method comprising delivering to a canine a composition comprising a first and a second androgenic prohormone wherein at least one of said first and said second androgenic prohormone is selected from the group consisting of: DHEA, 7-keto DHEA, pregnenolone, androstenedione, androstenediol, and DHEA-S.

16. The method of claim 15 wherein said composition is delivered in the format of a chewable edible treat.

17. The method of claim 15 that results in slowing or reversing one or more health declines associated with aging.

18. The method of claim 17 wherein said one or more health declines is selected from the group consisting of: increased obesity, arthritis, reduced bone density, cardiomyopathy, joint dysplasia, diabetes, blindness, and gum disease.

19. The method of claim 15 wherein said canine comprises a hepatic portal system and a liver wherein the hepatic portal system carries prohormone in said composition safely through the liver to systemic circulation.

* * * * *